United States Patent [19]

Quertermous et al.

[11] Patent Number: 5,288,846
[45] Date of Patent: Feb. 22, 1994

[54] CELL SPECIFIC GENE REGULATORS

[75] Inventors: Thomas Quertermous, Cambridge; Mu-En Lee, Boston, both of Mass.

[73] Assignee: The General Hospital Corporation, Boston, Mass.

[21] Appl. No.: 924,396

[22] Filed: Aug. 3, 1992

Related U.S. Application Data

[63] Continuation of Ser. No. 598,890, Oct. 19, 1990, abandoned.

[51] Int. Cl.$^5$ .................. C12N 15/85; C12N 15/67; C12N 5/16; C07H 21/04
[52] U.S. Cl. .................. 435/172.3; 435/240.2; 435/320.1; 536/241; 935/6; 935/33; 935/34; 935/36
[58] Field of Search .................. 536/24.1; 435/320.1, 435/240.2, 172.3, 69.1; 935/6, 33, 34, 70, 8

[56] References Cited

PUBLICATIONS

D. B. Wilson, et al. (1990) Molecular & Cellular Biology 10:4854–4862.
M. —E. Lee, et al., (1990) Journal of Biological Chemistry 265:10446–10450.
K. D. Bloch, et al. (1989) Journal of Biological Chemistry 264:10851–10857.
A. Inoue, et al. (1989) Journal of Biological Chemistry 264:14954–14959.
A.—J. van Zonneveld, et al. (1988) Proc. Natl. Acad. Sci., USA 85:5525–5529.
J. M. Wilson, et al. (1989) Science 244:1344–1346.
Beato, M. Cell 56:335–344 (1989).
Berliner et al., Blood 67(4):914–918 (1986).
Bodner et al., Cell 55:505–518 (1988).
Boulet et al., Proc. Natl. Acad. Sci. USA 83:3599–3603 (1986).
Dialynas et al., Proc. Natl. Acad. Sci. USA 83:2619–2623 (1986).
Dignam et al., Nucleic Acids Research 11(5):1475–1489 (1983).
Dynan, W. S. Cell 58:1–4 (1989).
Evans et al., Cell 58:877–885 (1989).
Frain et al., Cell 59:145–157 (1989).
Ingraham et al., Cell 55:519–529 (1988).
Inoue et al., Proc. Natl. Acad. Sci. 86:2863–2867 (1989).
Leiden et al., Immunogenetics 27:231–238 (1988).
Maniatis et al., Science 236:1237–1245 (1987).
Paigen et al., Atherosclerosis 57:65–73 (1985).
Russell et al., J. Biol. Chem. 205(5):2569–2575 (1990).
Strauss et al., Science 237:1217–1219 (1987).
Takuwa et al., J. Biol. Chem. 264(14):7856–7861 (1989).
Tsai et al., Nature 339:446–451 (1989).
Yanagisawa et al., Nature 332:411–415 (1988).
Zweibel et al., Science 243:220–222 (1989).

Primary Examiner—Robert A. Wax
Assistant Examiner—Gabrielle E. Bugaisky
Attorney, Agent, or Firm—Sterne, Kessler, Goldstein & Fox

[57] ABSTRACT

Methods and compositions for cell-specific expression of genes are provided. The invention utilizes the endothelin-1 promoter and promoter elements to direct expression of heterologous genes in endothelial cells. The promoters and elements are useful for directing cell-specific expression of therapies for vascular and cardiovascular diseases.

15 Claims, 5 Drawing Sheets

```
                A                              I-204CAT
    GCAGGTTTAG CAAAGGTCTC TAATGGGTAT TTTCTTTTTC TTAGCCCTGC CCCCGAATTG  -191
                                                  ^
                                              I-143CAT
    TCAGACGGCG GCGTCTGCCT CTGAAGTTAG CAGTGATTTC TTTCGGGCCT GGCCTTATCT  -131

I-129CAT            ********   I-98CAT
    CCGGCTGCAC GTTGCCTGTT GGTGACTAAT AACACAATAA CATTGTCTGG GGCTGGAATA  -71
                                                  ^
                            I-43CAT
    AAGTCGGAGC TGTTTACCCC CACTCTAATA GGGGTTCAAT ATAAAAAGCC GGCAGAGAGC  -11

TGTCCAAGTC AGACGCGCCT CTGCATCTGC GCCAGGCGAA CGGGTCCTGC GCCTCCTGCA   50

GTCCCAGCTC TCCACCGCCG CGTGCGCCTG CAGACGCTCC GCTCGCTGCC TTCTCTCCTG  110
                                                                     Bgl2
    GCAGCGCTGC CTTTTCTCCC CGTTAAAGGG CACTTGGGCT GAAGGATCGC TTTGAGATCT  170  [SEQ ID NO:1]
```

```
                          A
                          GCAGGTTTAG CAAAGGTCTC TAATGGGTAT TTTCTTTTTC TTAGCCCTGC CCCCGAATTG  -204CAT    -191
                                                                               ^
                                                                                            |-143CAT
TCAGACGGCG GCGTCTGCCT CTGAAGTTAG CAGTGATTTC TTTCGGGCCT GGCCTTATCT                           -131
|-129CAT              ********        |-98CAT
CCGGCTGCAC GTTGCCTGTT GGTGACTAAT AACACAATAA CATTGTCTGG GGCTGGAATA                           -71
                                            ^
           |-43CAT
AAGTCCGAGC TGTTTACCCC CACTCTAATA GGGGTTCAAT ATAAAAACCC GGCAGAGAGC                           -11

TGTCCAAGTC AGACGGCCCT CTGCATCTGC GCCAGGCGAA CGGGTCCTGC GCCTCCTGCA                            50

GTCCCAGCTC TCCACCGCCG CGTGCCCCTG CAGAGCGCTC CCTCGCTGCC TTCTCTCCTG                            110
                                                              Bgl2
GCAGCCCTGC CTTTTCTCCC CGTTAAAGGG CACTTGGGCT GAAGGATCGC TTTGAGATCT                            170 [SEQ ID NO:1]
```

FIG.1A

CELL SPECIFIC GENE REGULATORS

Statement of Government Rights in the Invention

This invention was made with government support under Grant 5 T32 HL07208-14 awarded by the National Institutes of Health. The government has certain rights in the invention.

This application is a continuation of application Ser. No. 07/598,890, filed Oct. 19, 1990, now abandoned.

Field of the Invention

The invention relates to the area of gene expression, particularly to regulation of gene expression in endothelial cells.

BACKGROUND OF THE INVENTION

The endothelium is found in lymphatic vessels, blood vessels, and the lining of the heart (endocardium). The circulatory system is lined with a thin layer of endothelial cells, extending from the heart through the arteries into the capillaries and back again through the veins. Thus, the endothelium plays an important role in vascular function.

The vascular endothelium is believed to play a key role in thrombosis, thrombolysis, lymphocyte homing, soft tissue inflammation and modulation of the immune response. Endothelial cells also play a major role in capillary transport, the regulation of plasma lipids as well as the control of hemostastis.

The recent characterization of the potent peptide vasoconstrictor endothelin-1 (ET-1) has expanded the understanding of the role of the endothelium in the regulation of vascular tone. Endothelin-1 is a 21 amino acid potent vasoconstrictor and growth factor produced by vascular endothelial cells. The vasoconstrictor is derived from amino acids 53–73 of a 203-amino acid precursor, preproendothelin (Bloch et al., *J. Biol. Chem.* 264:18156–18161 (1989)). The potent vasopressor has a prolonged duration of action. It induces mitogenesis and increases the expression of protooncogenes in vascular smooth muscle cells, fibroblasts, and mesangial cells. Other actions attributed to ET-1 include causing the release of atrial natriuretic factor from atrial cardiocytes in culture and inhibiting the release of renin from glomeruli. The effects of ET-1 on vascular smooth muscle cells implicate it in the pathogenesis of atherosclerosis and hypertension. Thus, knowledge about the regulation of ET-1 gene expression is fundamental to the understanding of the role of the peptide in vascular disease processes. (See Inoue et al., *Proc. Natl. Acad. Sci. USA* 86:2863–2867 (1989); Yanagisawa et al., *Nature* 332:411–415 (1988); Komura et al., *FEBS Lett.* 238:249–252 (1988); and Takuwa et al., *J. Biol. Chem.* 264:7856–7861 (1989).

During cellular differentiation, different cell types acquire the ability to stably express characteristic sets of genes. The molecular mechanism by which this occurs is poorly understood. In particular, little is known about the mechanisms of expression of endothelial cell-specific genes.

Accordingly, the ability to control gene regulation within the endothelial cells provides the opportunity for modulating vascular and cardiovascular systems.

SUMMARY OF THE INVENTION

Promoters and promoter elements for cell specific expression of genes, particularly gene expression in endothelial cells, are provided. The promoter and promoter elements are also capable of regulating the expression of heterologous promoters in a cell specific manner. Methods, vectors, and model systems for use of the promoter and promoter elements are provided.

DESCRIPTION OF THE FIGURES

FIG. 1. B, functional analysis of human ET-1 promoter by transfection of reporter CAT constructs. Serial deletion fragments of the ET-1 5′-flanking sequence were cloned into pOCAT1, and the plasmids were transfected into BAEC. All CAT constructs were co-transfected with pRSVβGAL, and relative CAT units were calculated as described under "Experimental Procedures." Constructs −4.4kCAT, −1.7kCAT, −0.7kCAT, −204CAT and −143CAT all expressed similarly high levels of CAT activity. Construct −129CAT, which lacks only the first 14 bp of the 5′ end of −143CAT, had approximately 40-fold less activity than −143CAT. Constructs containing less ET-1 5′-flanking sequence, −98CAT and −43CAT, revealed similar low levels of activity. Plasmid R-4.4kCAT, which contained the 4.4-kb ET-1 5′ sequence cloned in reverse orientation, served as negative control; plasmid pSV₂CAT served as positive control.

DETAILED DESCRIPTION OF THE INVENTION

Figure 1B:
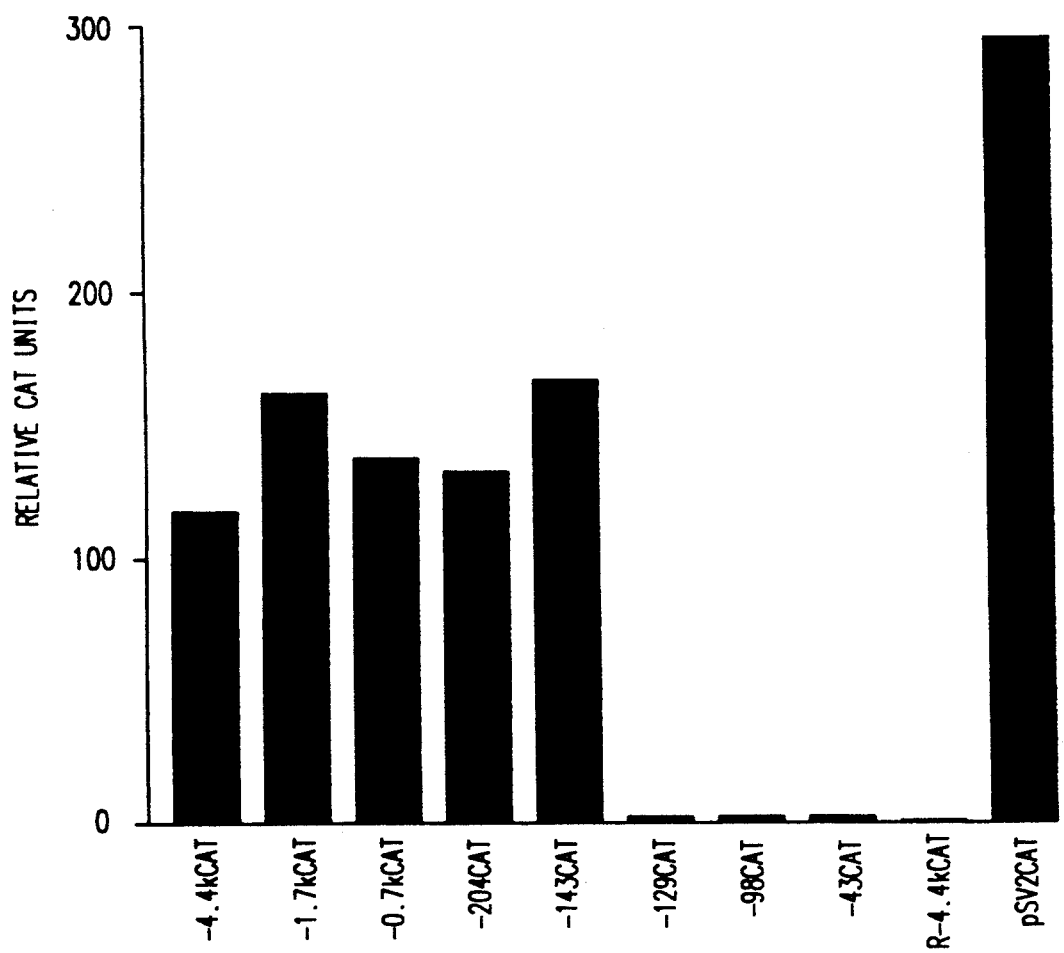
FIG. 1. A, nucleotide sequence of the endothelin-1 promoter region [SEQ ID NO: 1]. The genomic cloning and dideoxy chain termination sequencing were reported previously (Bloch, K. D., et al., *J. Biol. Chem.* 264:10851–10857 (1989)). The transcription start site, as determined by primer extension$^{FN}$ and S1 nuclease analysis (Inoue, A., et al., *J. Biol. Chem.* 264:14954–14959 (1989)), is indicated by the arrow (→), and nucleotides are numbered from this point of reference. CAAT and TATA consensus sequences are boxed: an AP1 consensus sequence is indicated by asterisks. The 5′-most nucleotide of various CAT constructs is indicated by vertical bars. Nucleotide sequence included in synthetic oligonucleotides and termed Region A is underscored and is listed as SEQ ID NO:2. Region B is the sequence between nucleotides −129 and −98 and is listed as SEQ ID NO:3. Carets at −204 and −86 bp indicate the 119-base pair fragment used in heterologous promoter experiments.

Compositions and methods for cell specific regulation of genes are provided. In particular, promoters and promoter elements which are capable of directing the rate and tissue specificity of gene expression are disclosed. More particularly, the promoter and promoter elements are capable of high levels of gene expression, specifically in endothelial cells.

The promoter region or DNA segment of the present invention comprises the promoter region of the endothelin-1 gene. This ET-1 promoter region has been cloned and sequenced and the nucleotide sequence is given in FIG. 1.

The nucleotide sequence of the promoter region or elements thereof can be operably linked to the coding region of any gene of interest to express that gene selectively in endothelial cells. As shown below in the Experimental section, this DNA segment is capable of inducing high levels of gene expression. For the most part, constructs containing the promoter sequence of the present invention show an increase in transcription of at least approximately 5-fold in endothelial cells, generally about 8-fold in endothelial cells compared with control promoters.

The present invention encompasses the entire ET-1 promoter as well as particular sequences (elements) of the ET-1 promoter region. These elements are capable of directing high rates of gene transcription and of directing tissue specific expression. The elements can be used with portions of the ET-1 promoter or alternatively with heterologous promoters or heterologous promoter regions to control transcription in a cell specific manner.

While the nucleotide sequence of the promoter (including the promoter elements) are given in FIG. 1 and reference is made to such sequence in the specification, it is recognized that nucleotide substitutions can be made which do not affect the promoter or promoter element function. The present invention encompasses such nucleotide sequences.

By "cell specific expression" is intended that the promoters or promoter elements direct expression in particular cell types. That is, the ET-1 promoter and the promoter elements disclosed herein direct expression of a gene in endothelial cells. Thus, the invention provides a means to target expression of a particular gene in endothelial cells while avoiding expression in other cells.

To express a gene of interest, the promoter or promoter elements are operably linked to the gene. By operably linked is intended operably linked for promoter and elements. For high expression of selective gene expression in endothelial cells, constructs containing a promoter element comprising at least about 143 bp of the promoter region operably linked to a gene of interest, are capable of producing high levels of gene expression. In particular, regions of the promoter from about bp −204 to about −86 [SEQ ID NO:4 or fragment thereof] when operably linked to a heterologous gene or coding sequence are capable of inducing high levels of transcription. That is, promoter elements comprising this 143 bp sequence are capable of directing transcription of a promoterless gene or coding sequence.

An "operably linked" ET-1 promoter or promoter element will direct the transcription of a nucleic acid molecule joined in proper reading frame. With regard to heterologous promoters, the promoters and elements of the invention are operably linked when they control the function of such heterologous promoters, that is, the elements direct expression of the promoter, particularly in endothelial cells.

As indicated, however, promoter elements of the invention can also be utilized to direct expression of heterologous promoters. When utilized in this manner, the ability to control foreign or heterologous promoters is independent of the orientation of the promoter element DNA. That is, the promoter element DNA is functional when placed in either 5' to 3' or 3' to 5' orientation with respect to the gene being expressed.

Thus, the sequences of the ET-1 promoter between about base pair −86 and about −204 [SEQ. ID NO:4] can be used to increase the rate of transcription in a tissue-specific fashion. The sequences are functional in either 5' to 3' or 3' to 5' direction when directing heterologous promoter expression, and are similar in this regard to other cis-acting sequences that mediate tissue-specific transcription and other cell types. See, for example, Boulet et al. 1986 *Proc. Natl. Acad. Sci. USA*, 83:3599–3603; Dynan 1989 *Cell* Volume 58 pages 1–4; Evans et al. 1989 *Cell* Volume 58, 877–885; Frain et al. 1989 *Cell* Volume 59 145–157; Ingraham et al. 1989 *Cell* Volume 55 529–529; and, TSAI et al. 1989 *Nature* Volume 339 446–451.

When using the promoter or promoter element to direct expression of a heterologous promoter, the promoter element is generally placed within a few nucleotides of the promoter of interest. Generally, the promoter element is placed within about 10 kb of the heterologous promoter, more generally within about 200 nucleotides of the heterologous promoter.

It is further recognized that other elements comprising specific regions within the ET-1 promoter, more specifically, within the 143 bp element are important for tissue specific expression. One such element comprises at least about 119 bp. This element comprises the nucleotide sequence of the ET-1 promoter from about −204 to about −86 [SEQ ID NO:4]. This element is able to confer an endothelial cell-specific positive effect on the rate of transcription of heterologous promoters or promoter regions.

Other promoter elements include regions of the ET-1 promoter denoted Regions A and B (see FIG. 1). Region A comprises nucleotides of the ET-1 promoter from about base pair −117 to about −148 [SEQ ID NO: 2]. Region A contains positive regulatory sequences that function in conjunction with other elements of the ET-1 promoter in a stimulatory fashion. In fact, the data shows that Region A interacts with a second region (Region B) which comprises promoter nucleotides from about base pair −98 to about −129 [SEQ ID NO: 2] to induce high rates of transcription of genes under their control. These positive regulatory elements also direct expression in a cell-specific manner.

It is recognized that other elements or nucleotide sequences within the ET-1 promoter region may be important for cell-specific expression. The present invention encompasses such elements. For example, a positive regulatory element may be found in the 14 bp element between −143 and −129 of the ET-1 promoter as when this element is deleted from the 143 bp element a dramatic decrease in transcription is observed.

Further, specific nucleotides or regions within the promoter elements may be identified as necessary for regulation. These regions of nucleotides may be located by fine structural dissection of the elements, particularly Region A and Region B, can be studied by experiments which analyze the functional capacity of a large number of promoter mutants. Single base pair mutations that preserve the relative orientation of A, and B, and the CAAT and TATAAA elements can be generated utilizing polymerase chain reaction (PCR) technology. (See U.S. Pat. No. 4,683,202.) Oligonucleotides are then designed that code for the regions of interest, except that single base pair changes will be made in the region that is under examination. In this fashion, a number of mutated promoter regions are amplified, and then cloned back into reporter constructs and evaluated with transfection and CAT assay techniques (as set forth in the Experimental section below). These amplified fragments can be cloned back into the context of the ET-I promoter and also into the heterologous promoter constructs. In this fashion, the exact nucleotide sequences that are important in directing the endothelial cell transcription of the gene are identified.

This analysis will also identify nucleotide changes which do not effect promoter function. Thus, functional derivative promoters and promoter elements can be constructed.

Factional analysis of the promoter region can be facilitated by footprint and gel-shift studies. Knowledge of the exact base pairs important in mediating binding of proteins provides evidence of bases important in mediating the transcriptional response. Sequences found to have impaired function can be used to design oligonucleotides for use as competitors in footprinting and gel shift experiments (for details, see Experimental section, below). Thus a correlation can be made between function of the cis-acting sequence and proteins binding to this sequence.

The invention further encompasses the base pairs important in DNA-protein interaction. Such base pairs can also be elucidated. In this manner, genomic fragments containing the −143 to −129 [SEQ ID No: 5] sequence and fragments containing other areas of interest will be employed in in vitro foot-printing experiments (Galas et al., *Nucleic Acids Res.* 9:6505–6525 (1981)). Isolated restriction fragments are radiolabeled and subsequently incubated with nuclear extracts made with established techniques (for example, Dignam et al., *Nucleic Acids Res.* 11:1475–1489 (1983)). Nuclear extracts (containing DNA binding proteins) can be made from bovine aortic endothelial cells. Control cell extracts include NIH-3T3 mouse fibroblasts, HeLa cells, and a human T cell line (Juikat). Labeled DNA fragments are incubated with the nuclear extracts, digested with DNAse I, and electrophoresed on a denaturing polyacrylamide gel. DNA binding proteins in the cell extract bind to their recognition sequence contained in the labeled restriction fragment, and protect the DNA from digestion by the DNAse. Regions of protection delineate the binding site.

A number of measures can be taken to decrease nonspecific DNA protein interaction, including the addition of poly d(IC). Competition experiments can also be conducted with both specific and nonspecific cold DNA. Maxam and Gilbert sequencing reactions of the fragment can be used as a marker to define the nucleotides protected from DNAse digestion.

The invention is further drawn to the identification and characterization of trans-acting factors which interact with the promoter or promoter elements. Cis-acting regulatory sequences serve as binding sites for proteins which are termed trans-acting factors (TAF) (Dynan W. S., Tjian T. Nature 1985; 316:774–778; Maniatis T., Godburn S., Fischer J. A. Science 1987; 236:1237–1245.). Each gene is presumed to bind one or more proteins at each of its regulatory sequences, and these proteins interact with one another and RNA polymerase II in a fashion that rigidly controls transcription. It is currently assumed that proteins binding to distant regulatory sequences are brought into the proximity of the promoter region by looping out of the intervening DNA.

TAFs have been identified in nuclear extracts by their ability to bind to and retard electrophoretic mobility of cis-acting sequence DNA fragments (Dignam J. D., Lebovitz R. G., Roeder R. G. Nucleic Acids Res. 1983; 11:1475–1489. 12.-Dynan, W. 5. (1989) Cell 58, 1–4; Fletcher C., Heintz N., Roeder R. G. Cell 1987; 773–781; Scheidereit C., Heguy A., Roeder R. G. Cell 1987; 51:783–793).

The cis-acting sequences are useful in gel retardation assays to determine binding activity in nuclear extracts. The technology for gel shift assays is well described in the literature and includes many of the same reagents used in footprint experiments (Fried M., Crothers D. M. Nucleic Acids Res. 1981; 9:6505–6525; Revzin A. Biotechniques 1989; 7:346–355; Strauss F. A., Varshavsky A. Cell 1984; 37:889–901.). Either $^{32}$P-labeled restriction fragments or annealed pairs of complementary oligos are incubated with nuclear extracts and poly d(I-C) in a binding buffer, and the products of this reaction electrophoresed on a non-denaturing polyacrylamide gel. The location of the DNA fragment on the gel as determined with autoradiography is retarded in cases where protein has bound to the DNA. The extent of the retardation is a relative function of the size of the protein, and it has thus been possible to distinguish two or more different proteins present in different tissues binding to a single sequence.

For control experiments, competition assays performed with oligonucleotides carrying the native sequence and mutations shown to affect the functional profile of the DNA element can be performed. Nuclear extracts are made from bovine aortic endothelial cells, as well as NIH-3T3, HeLa, and Jur-kat cells. Therefore, it is possible to determine if proteins binding to this region are cell-type specific.

In some cases, cis-acting regulatory elements are the site for assembly of multi-subunit protein complexes. A specific example is the consensus sequence that appears to mediate binding of heterodimeric complexes (Chodosh I. A., Baldwin A. S., Carthew R. W., Sharp P. A. Cell 1988; 53:11-24.). While this appears not to be the case with many tissue-specific enhancers studied thus far, small scale purification and fractionation steps can be performed to investigate this possibility.

Binding proteins can be purified by using heparinagarose and DNA affinity columns (Ausubel P. M., Brent R., Kingston R. E., Moore D. D., Seidman J. G., Smith J. A., Struhl K., editors: Current Protocols in Molecular Biology. New York, John Wiley and Sons 1987; Bodner M., Karin M. Cell 1987; 50:267-275; Fletcher C., Heintz N., Roeder R. G. Cell 1987; 773-781; Kadonaga J. T., Carner K. R., Masiarz F. R., Tijan R. Cell 1987; 51:1079-1090; Scheidereit C., Heguy A., Roeder R. G. Cell 1987; 51:783-793.). For purification, DNA-cellulose chromatography can be utilized, followed by affinity chromatography utilizing the cognate DNA sequence attached to a matrix. Fractionation of extracts containing the binding activity will employ phosphocellulose chromatography (Chodosh I. A., Baldwin A. S., Carthew R. W., Sharp P. A. Cell 1988; 53:11-24.). Binding activity during these procedures are monitored by gel shift assay.

Once the trans-acting factors have been identified they can be cloned by techniques available in the art. The large scale production of native and mutated TAFs will be possible by cloning of the genes coding for these proteins. The general methods for cloning proteins are known in the art. First, a small region of protein sequence using microsequencing technology is obtained. A degenerate or "best guess" oligonucleotide is then synthesized, labeled, and used as a probe to screen a cDNA library constructed from cells known to make the protein (Lathe R. J. Mol. Biol. 1985; 183:1-12.). Second, purified-protein or partially purified protein may be used as an immunogen, and polyclonal antisera used for immunoscreening of an expression library in a vector such as λgtll (Young P. A., Davis P. W. Science 1983; 222:778-782; Beato M. Cell 1989; 56:335-344).

A number of TAFs have been cloned by screening an expression cDNA library using a radiolabeled oligonucleotide representing the consensus binding recognition site (reviewed in Singh et al., *Biotechniques* 7:252-261 (1989)). The technology is quite similar to that described for immunoscreening (Young P. A., Davis P. W. Science 1983; 222:778-782; Beato M. Cell 1989; 56:335-344.), except that a 32P-labeled double-stranded oligo is used as a probe instead of an antibody. Clones that contain and are able to express the DNA binding domain of the TAF recognize and bind the labeled oligo and thus are identified on an autoradiograph. Refinement of this technique has indicated that improved sensitivity is achieved with catenated probes and with denaturation and renaturation of the expressed protein on the nitrocellulose filters (Singh H., Clerc R. G., LeBowitz J. H. Biotechniques 1989; 7:252-261.).

A λgtll HUVEC cDNA expression library is available that has been used to clone a number of endothelial cell cDNAs (Ginsburg D., Hcindin R. I., Bonthron D. T., Donlon T. A., Bruns C. A. P., Latt S. A., Orkin S. Science 1985; 228:1401-1406.). This library was generated using random primers (not oligo dT). Thus, the library contains the DNA binding sequence as it was made independently of which portion of the protein is responsible for DNA binding (Singh H., Clerc R. G., LeBowitz J. H. Biotechniques 1989; 7:252-261).

Once a cDNA clone is available it can be used in an *E. coli* based expression system to produce large quantities of the putative binding protein (Bodner M., Castrillo J. -L., Theill L. E., Deerinck T., Ellisman M., Karin M. Cell 1989; 55:505-518). Evidence that the clone codes for the binding protein of interest will come from the use of the expressed protein to protect the regulatory element in footprinting assays and specifically bind and retard mobility of the DNA in a gel shift assay. More definitive proof will require that the protein be able to increase the transcription rate of a promoter region linked to the cognate cis-acting regulatory sequence. This could be accomplished by adding recombinant TAF to an in vitro expression system. Such systems have been useful when purified protein but no clone is available (Bodner, M., Karin M., *Cell* 50:267-275 (1987); Dignam, J. D., Lebovitz, R. G., Roeder, R. G., *Nucleic Acids Res.* 11:1475-1489 (1983); Dynan, W. S., *Cell* 58:1-4 (1989)).

Availability of a cDNA clone coding for the TAF allows gene transfer experiments that assess the ability of the cloned protein to confer on a cell the ability to transcribe genes that it normally cannot transcribe. This type of experiment allows analysis of the structure-function relationships of the TAF.

Constructs coding for various mutated TAFs can be put into HeLa cells in conjunction with a heterologous promoter-CAT construct containing the cognate cis-acting DNA sequence. The ability of these proteins to promote transcription of the reporter gene can be evaluated, and information thus obtained about the functional domains of the protein. This type of methodology has been used very effectively to determine the structure-function relationships of the steroid receptors (reviewed in Beato, M., *Cell* 56:335-344 (1989)).

The promoters and promoter elements also find use in transgenic studies. Transgenic mice have provided a powerful genetic model for the study of a number of human diseases including cancer. They have also provided an important in vivo method for studies of gene regulation that have confirmed and extended observations made with transfection reporter gene experiments (Palmiter F. L., Ilrinster F. L. Ann. Rev. Genet. 1986; 20:465-499.). Studies aimed at dissecting the signals allowing developmental relation of gene expression can rarely be performed in cell culture models and is probably best studied with a transgenic model. This type of experiment is possible because of the remarkable conservation between species of regulatory sequences, such that human regulatory signals are accurately interpreted by the mouse transcription machinery.

Constructs expressed in transgenic mice could provide much information about the regulation of the ET-1 gene. Thus, reporter gene constructs are assembled containing various regions of the ET-I promoter upstream of the lacZ gene of *E. coli*. The lacZ gene has been extensively used as a marker for gene expression in vivo by incubating tissue slices in a solution of X-gal and visualizing the resulting blue color by light microscopy (Goring D. R., Rocsant J., Clapoff S., Breitman N. L., L. -C. Tsui. Science 1987; 235:456-458.). By studying different tissues at different points in development, information about the developmental regulatory sequences included in the construct can be gained.

One such transgenic construct contains 4.4 kb of ET-1 promoter driving the lac Z gene. While in vitro experiments have shown that the promoter elements important for transcription of this gene in cells in culture are included in the 200 bp upstream of the start site, we have no information about developmental regulatory sequences, or about sequences that allow expression in cells of the central nervous system. This construct was shown to be functional when transfected into bovine endothelial cells in culture.

Transgenic mice can be made by methods known in the art. Generally, the DNA constructs of interest are microinjected into mouse embryos. Generally, methods are available in the art for the production of transgenic animals. The most widely used method through which transgenic animals have been produced involve injecting a DNA molecule into the male pronucleus of a fertilized egg (Brinster et al., *Cell* 27:223 (1981); Costantini et al., *Nature* 294:982 (1981); Harpers et al., *Nature* 293:540 (1981); Wagner et al., *Proc. Natl. Acad. Sci. USA* 78:5016 (1981); Gordon et al., *Proc. Natl. Acad. Sci. USA* 73:1260 (1976)).

Once the DNA molecule has been injected into the fertilized egg cell, the cell is implanted into the uterus of recipient female and allowed to develop into an animal. Thus, all of the cells of the resulting animal should contain the introduced gene sequence.

Alternatively, transgenic animals may be produced by incorporating a desired gene sequence into a virus which is capable of infecting the cells of a host animal. See, Elbrecht et al., *Molec. Cell. Biol.* 7:1276 (1987); Lacey et al., *Nature* 322:609 (1986); Leopol et al., *Cell* 51:885 (1987).

Further, pluripotent embryonic stem cells may be injected into a blastocyst of a developing embryo and proliferate and differentiate. See, Robertson et al., *Cold Spring Harb. Conf. Cell Prolif.* 10:647 (1983); Bradley et al., *Nature* 309:255 (1984); Wagner et al., *Cold Spring Harb. Symp. Quant. Biol.* 50:691 (1985).

The resulting transgenic mice or founders can be bred and the offspring analyzed to establish lines from the founders that express the transgene. In the transgenic animals, multiple tissues can be screened to observe for endothelial cell and parenchymal cell expression. RNA studies in the various transgenic mouse lines will allow evaluation of independence of the integration site to expression levels of the transgene. A murine ET-I cDNA, and a probe for the lacz gene can be utilized in RNA studies to allow comparison of the level of expresionn of the transgene with the innate gene. Histochemical determination of tissue specific expression of the transgene and the innate gene are compared at various developmental points. The transgene will be detected with X-gal and ET-I expression with a commercially available polyclonal antisera (Peninsula). Discrepancies between expression of innate ET-I and the transgene will indicate regulatory regions not included in the constructs, and will require the addition of more flanking sequence in the constructs. See Hogan B., Constantini F., Lacy E., *Manipulating the mouse embryo: a laboratory manual*, Cold Spring Harbor Press, Cold Spring Harbor, N.Y. (1986).

The transgenic constructs are useful for models of vascular disease. A number of growth factors, cytokines, and inflammatory mediators have been implicated in various stages of vascular diseases. Presumably, expression of these genes is limited in the normal state, and initiated or increased in the pathological situation. Thus constitutive over-expression of particular genes would mimic the pathologic state and provide a useful animal model.

Targeted over-expression of transgenes has allowed unique insight into physiological and pathological processes. Specifically, the invention provides for the targeting of over-expression of growth factors, cytokines, endothelin and other genes in the vessel wall of transgenic mice to develop models for the study of vascular disease. The transgenic animals can also be utilized as a model of vascular disease to evaluate potential therapeutic agents. For example, the development of atherosclerosis in mice has been studied. Utilizing the methods of the invention, overexpression of cytokines on the rate of development of this disease can be studied (Paigen B., Morrow A., Brandon C., Mitchell D., Holmes P. Atherosclerosis 1985; 57:65–73.). Mice which develop vascular disease would then serve as a model for the study of therapeutic modalities.

The ET-1 promoter and promoter elements provide a useful means for carrying out gene therapy. That is, the regulatory elements can be utilized to target over-expression of candidate gene in the vascular wall. The promoter or promoter elements can be used to express any gene, particularly those genes whose gene product is needed in endothelial cells.

In this manner, constructs comprising the promoter or promoter elements can be utilized for drug delivery, particularly those drugs or agents involved in thrombosis, thrombolysis, inflammation, modulation of the immune response, and the like. More specifically, the promoter and elements can be used to express Von Willebrand's factor: plasminogen activator or other factors to affect clotting; proteins directed to disease deficiencies of blood-borne proteins; proteins directed to other deficiencies, such as liver proteins; agents to combat hypercholesterol, including drugs as well as overexpression of the LDL receptor, etc.

For the most part, constructs comprising the promoter or promoter elements will be utilized to target gene expression in endothelial cells. Any means available in the art for transfer of the constructs into animals, including humans, can be utilized. This includes viral vectors, particularly retroviral vectors (see, for example, Zweibel et al., *Science* 243:220 (1989), and the references cited therein), as well as other methods.

The following examples are offered by way of illustration and not by way of limitation.

EXPERIMENTAL

Experimental Procedures

Cell Culture—Bovine aortic endothelial cells (BAEC) were isolated and cultured in Dulbecco's modified Eagle's medium supplemented with 10% fetal calf serum (Hyclone), 600 µg of glutamine/ml, 100 units of penicillin/ml, and 100 µg of streptomycin/ml as described (Blaconi, G., et al., *Med. Biol.* (Helsinki) 64:231–245 (1986)). The BAEC were passaged every 3 to 5 days; cells from passages 7 through 10 were used for transfection experiments. NIH-3T3 fibroblasts and HeLa cell lines were obtained from the American Type Culture Collection and cultured in conditions identical with those for the BAEC.

Plasmids and Synthetic Oligonucleotides. The transcription start site of the human ET-1 gene has been determined by primer extension[FN] and by S1 nuclease analysis (Inoue, A., et al., *J. Biol. Chem.* 264:14954–14959 (1989)). Nucleotide pairs are numbered from this reference point (FIG. 1A). The BglII site used to generate deletion constructs is located 102 base pairs (bp) downstream of the transcription start site, in the first (untranslated) exon of the ET-1 gene.

Reporter fusion plasmids all employed the prokaryotic chloramphenicol acetyltransferase (CAT) gene in conjunction with ET-1 5'-flanking sequence. The β-galactosidase (βGAL) gene was employed in control plasmids driven by the Rous sarcoma virus (RSV) regulatory sequence. The plasmids pOCAT1 (Prost, E., et al., *Gene (Amst.)* 45:107–111 (1986)), pSPCAT (Leung, K., et al., *Nature* 333:776–778 (1988)), pSV$_2$CAT (Gorman, C. M., et al., *Mol. Cell. Biol.* 2:1044–1051 (1982)), and pRSVβGAL (Edlund, T., et al., *Science* 230:912–916 (1985)) have been described previously. The plasmid pSPI1CAT was kindly provided by J. M. Leiden, Howard Hughes Medical Institute, University of Michigan (Kaprinski, B. A., et al., *Mol. Cell. Biol.* 9:2588–2597 (1989)). A 4.4-kilobase (kb) XbaI-BglII human ET-1 genomic fragment (Bloch, K. D., et al., *J. Biol. Chem.* 264:10851–10857 (1989)) was cloned in the appropriate (−4.4 kCAT) and reverse (r−4.4 kCAT) orientation upstream of the chloramphenicol actyltransferase gene in pOCAT1. The plasmids −1.7 kCAT and −0.7 kCAT were constructed by cloning 1.8-kb EcoRI-BglII and 0.8-kb SacI-BglII human ET-1 genomic fragments into the same cloning site of pOCAT1 in 5' to 3' orientation. Plasmids −204CAT, −143CAT, −129CAT, −98CAT, and −43CAT were generated by digesting the EcoRI-BglII fragment with exonuclease II from the 5' end and subsequently cloning the truncated fragments into pOCAT1 in the 5' to 3' orientation. These constructs shared a common 3' BglII site, but differed at the 5' end (located at base pair −204, −143, −129, −98, or −43). Two 42-bp complementary oligonucleotides encoding the sequence between bp −148 and −117 [SEQ ID NO:2] of the human ET-1 gene were synthesized and annealed. The oligonucleotides were designed such that the resulting DNA fragment had a BamHI site at one end and a BglII site at the other end. The synthetic fragment was cloned into plasmids −129CAT and −98CAT at a BamHI site immediately 5' of the ET-1 genomic fragments. Clones containing the oligonucleotides in the appropriate orientation [(−129+0)CAT, (−98+0)CAT] and clones containing the oligonucleotides in the reverse orientation [(−129+R0)CAT, (−98+R0)CAT] were isolated. A 119-bp fragment corresponding to sequence −204 to −86 [SEQ ID NO:4] was generated by digesting from the 3' end of the ET-1 genomic fragment in −204CAT with exonuclease III. This fragment was cloned into the SmaI site of pSPCAT in both orientations to generate constructs (−204.−86)pSPCAT and (−86.−204)pSPCAT. The authenticity of constructs −4.4kCAT, r−4.4kCAT, −1.7kCAT, and −0.7kCAT was verified by restriction mapping. Dideoxy chain termination sequencing with a synthetic oligonucleotide corresponding to sequence +52 to +75 allowed verification of the other constructs. Plasmid DNA was isolated by alkaline lysis followed by CsCl equilibrium centrifugation (Maniatis, T., et al., *Molecular Cloning: A Laboratory Manual*, Cold Spring Harbor Laboratory, Cold Spring Harbor, N.Y. (1982)).

Transfection and CAT Assays. All cell lines were transfected with 20 μg of the appropriate CAT construct plasmid DNA by the calcium phosphate method as previously described (Graham, F. L., et al., *Virology* 52:456–467 (1973)). To correct for variability in transfection efficiency, 10 μg of pRSVβGAL plasmid DNA was co-transfected in all experiments. Cell extracts were prepared 48 h after transfection by four cycles of freezing and thawing. Extracts were centrifuged, and supernatants were assayed for CAT and β-galactosidase activity. The CAT assay was performed by a modified two-phase fluor diffusion method (Neumann, J. R., et al., *BioTechniques* 5:444–447 (1987)). A reaction mixture containing [-C]acetyl coenzyme A (NEC −3131, 4.0 mCi/mmol) and 1M Tris-HCl (pH 7.8) was added to the cell extract to achieve a final volume of 0.25 ml and final component concentrations of 1.0 mM chloramphenicol, 0.1 mM acetyl coenzyme A, and 100 mM Tris-HCl. The reaction mixture was gently overlaid with 5 ml of a water-immiscible scintillation fluor (Econofluor, Du Pont) and then incubated at 37° C. for 2 h. Scintillation assays were performed in a Beckman counter. β-Galactosidase activity was assayed as described previously (Edlund, T., et al., *Science* 230:912–916 (1985)). Counts per min (CAT assay) or absorption at 410 nM (β-galactosidase assay) obtained with the experimental extracts were compared to standard curves produced with varying concentrations of purified *Escherichia coli* chloramphenicol acetyltransferase (1000 units/ml, Pharmacia LKB Biotechnology Inc.) and β-galactosidase (Sigma). In this way, the CAT and β-galactosidase activities in each extract were determined. The ratio of CAT activity to β-galactosidase activity in each sample served as a measure of normalized CAT activity. For each series of experiments in each cell line, the normalized CAT activity of each sample was divided by that of a control construct, and the quotient was expressed in relative CAT units. The construct r−4.4kCAT was used as control in all experiments except for those with the heterologous promoter, in which pSPCAT was used as a control. Each fusion construct was transfected at least three times, and each transfection was done in duplicate. Since there was little variation between experiments, the data are presented as the mean of duplicate transfections, for a single representative experiment.

RESULTS AND DISCUSSION

Functional Analysis of the ET-1 Promoter. To determine whether DNA sequences flanking the 5' end of the ET-1 gene were sufficient for expression in endothelial cells, a plasmid containing a large region of ET-1 upstream sequence in a CAT reporter construct (−4.4kCAT) was transfected into BAEC. This construct contained 4.4 kb of ET-1 5'-flanking sequence in conjunction with the prokaryotic chloramphenicol acetyltransferase (CAT) gene in the promoterless pOCAT1 plasmid (Prost, E., et al., *Gene (Amst.)* 45:107–111 (1986)). In the appropriate orientation, this 5'-flanking sequence of the ET-1 gene was able to induce a high level of CAT gene expression (520,000 cpm) above background (3,000 cpm) in BAEC (FIG. 1B). A construct containing the ET-1 5' sequence in the reverse orientation (R-4.4kCAT) was associated with minimal transcription (4,500 cpm, FIG. 1B). This difference suggested that positive regulatory elements within the 4.4-kb ET-1 5' genomic fragment were directing expression of the CAT gene in BAEC. Such regulatory elements would probably be important to expression of the gene in human endothelial cells.

To localize the sequences directing ET-1 gene expression, a series of deletion mutants was transfected into BAEC. Fusion plasmids containing smaller fragments of ET-1 5'-flanking sequence, −1.7kCAT, −0.7kCAT, −212CAT, and −143CAT, all promoted high levels of CAT gene expression, suggesting that the sequences of interest were located within a 143-base pair region 5' of the start site (FIGS. 1, A and B). Although plasmid −129CAT contained only 14 bp less promoter region sequence than −143CAT, it was associated with 40-fold lower CAT activity in transfected BAEC (FIGS. 1, A and B). Plasmids containing 98 and 43 bp of ET-1 promoter sequences had similarly low levels of CAT activity. These results suggested the presence of a positive regulatory element, at least a portion of which was contained in the 14 bp between −143 and −129.

Figure 2:
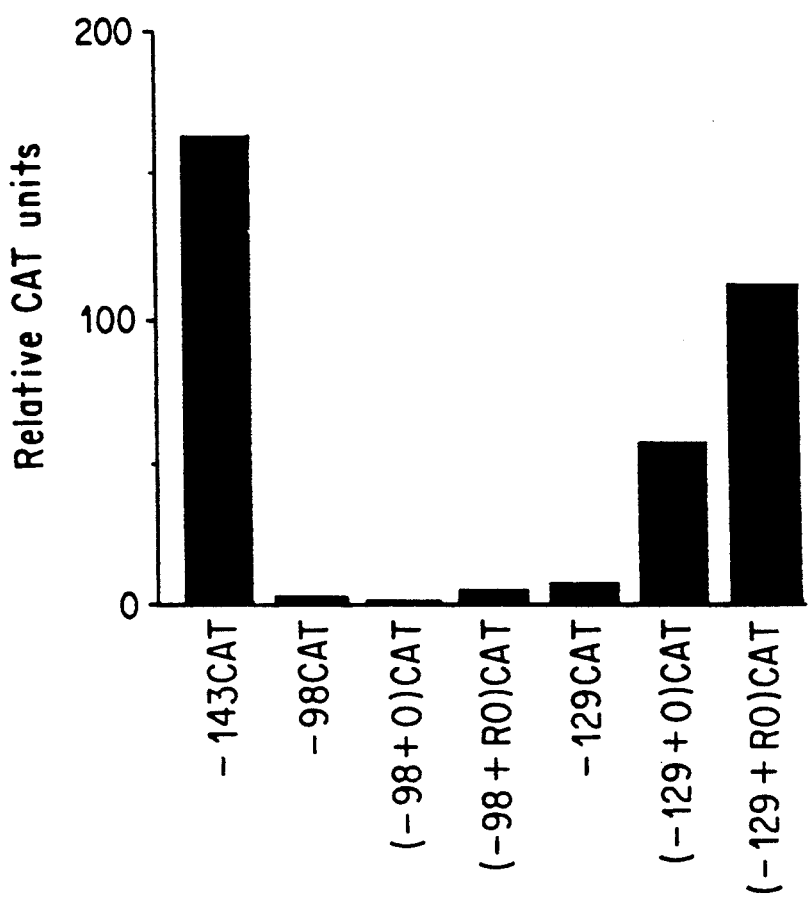
FIG. 2. Reconstitution experiments with oligonucleotides coding for Region A (bp −148 to −117[SEQ ID NO:2]). Complementary oligonucleotides coding for this region of the ET-1 promoter were cloned upstream of the ET-1 promoter region and were included in the poorly active −98CAT and −129CAT constructs in the correct orientations [(−98+0)CAT and (−129+0)CAT], and in the reverse orientations [(−98+R0)CAT and (−129+R0)CAT]. Activity of the −143CAT construct is shown to indicate maximal promoter function. Addition of Region A to −98CAT did not augment the transcriptional rate, whether the oligonucleotides were cloned in the correct or reverse orientation. When the oligonucleotides were cloned upstream of the −129CAT construct, they provided for ~7-fold increase in the rate of transcription in the correct orientation, and ~19-fold increase in the reverse orientation.

We further analyzed the functional role of the region between bp −129 and −143 [SEQ ID NO: 5] by using complementary oligonucleotides. The sequence encoded by these oligonucleotides (bp −148 to −117 [SEQ ID NO: 2]) was chosen to include bp −129 to −143 [SEQ ID NO: 5] and potentially important flanking sequences. The region of the promoter encoded by these oligos has been termed Region A (FIG. 1A). Oligonucleotides were annealed and cloned (in both orientations) upstream of the ET−1 promoter sequence in −98CAT and −129CAT. When the oligonucleotides were placed upstream of −98CAT, either in the correct [(−98+0)CAT] or reverse [(−98+R0)CAT] orientation, the level of CAT expression was similar to that of native −98CAT (FIG. 2). When the oligonucleotides were inserted into −129CAT in the correct [(−129+0)CAT] or reverse {(−129+R0)CAT] orientation, there was a marked increase in CAT expression compared with native −129CAT (FIG. 2). The construct [(−129+0)CAT] exhibited approximately 50% of the activity of −143CAT, while [(−129+R0)CAT] exhibited approximately 75% of the activity of −143CAT.

These results provide evidence that Region A contains positive regulatory sequences that function in conjunction with the remainder of the ET-1 promoter in a stimulatory fashion. In addition, the data suggest that Region A is not sufficient in itself to induce a high rate of transcription, but may interact with a second region which lies between bp −98 and −129 [SEQ ID NO: 3] (Region B). It is unlikely that these data represent the reconstitution of a single positive regulatory element around −129 bp, since the oligonucleotides are functional in the reverse orientation. It is possible that the activity of the oligonucleotides in −129CAT (relative to that in −98CAT) reflects a required spacing for Region A from one of the proximal promoter sequences, for instance the CAAT or TATAAA element. Site-directed mutagenesis of Region B or the analysis of constructs in which the spacing interval varies will be required to examine this possibility.

Figure 3:
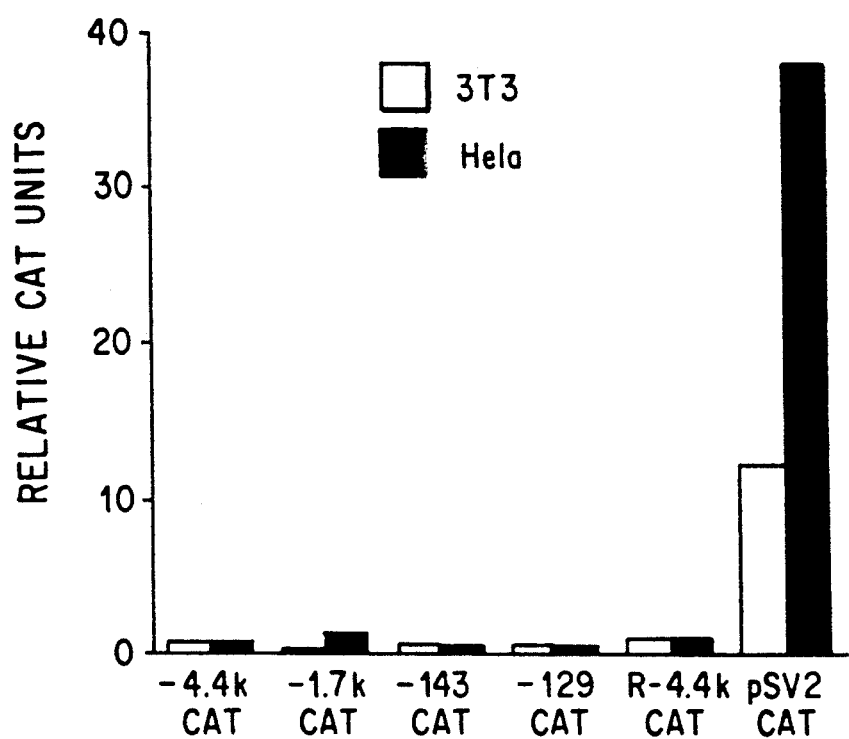
FIG. 3. The human ET-1 promoter has weak activity in NIH-3T3 and HeLa cells. Plasmid pSV₂CAT expressed significant CAT activity in both NIH-3T3 (white bars) and HeLa cells (black bars). However, CAT fusion plasmids containing representative deletion fragments of the ET-1 gene, −4.4kCAT, −1.7kCAT, −143CAT, and −129CAT, expressed low levels of CAT activity, similar to the negative control R-4.4kCAT FIG. 4. Effects of ET-1 5' sequence (bp −204 to −86[SEQ ID NO:4]) on the expression of the minimal SV40 promoter in pSPCAT. Constructs were transfected into BAEC (white bar), NIH-3T3 (hatched bar), and HeLa cells (black bar). Plasmid pSPCAT had minimal activity in all three cell types. Plasmid pSPIlCAT, which contained a universal enhancer in addition to the minimal SV40 promoter, revealed significantly greater CAT activity compared with pSPCAT in all three cell types (6- to 9-fold). Constructs containing ET-1 promoter sequence cloned upstream of the SV40 promoter in correct orientation [(−201.−86)CAT] or reverse orientation [−86.−204)CAT] showed ∼8-fold greater CAT activity in BAEC but not in NIH-3T3 or HeLa cells. Please note that the scale here is different from in previous figures.

Evidence for an Endothelial Cell-specific ET-1 Gene Promoter Sequence. To determine whether the positive regulatory elements of the ET-1 promotor are cell type-specific, fusion plasmids containing serial deletion mutants of the ET-1 gene 5'-flanking sequence were transfected into NIH-3T3 (fibroblast) and HeLa (epidermoid carcinoma) cells. In contrast to the high level of transcription of fusion plasmids −4.4kCAT, −1.7kCAT, and −143CAT in BAEC, these plasmids directed minimal transcription in NIH-3T3 and HeLa cells (FIG. 3). The high level of CAT activity associated with the transfection of pSV$_2$CAT in both cell types indicates that they can be transfected and generate CAT activity. These data indicate that the ET-1 sequence included in −143CAT contains regulatory elements capable of permitting transcription in BAEC but not in other cell types tested.

Figure 4:
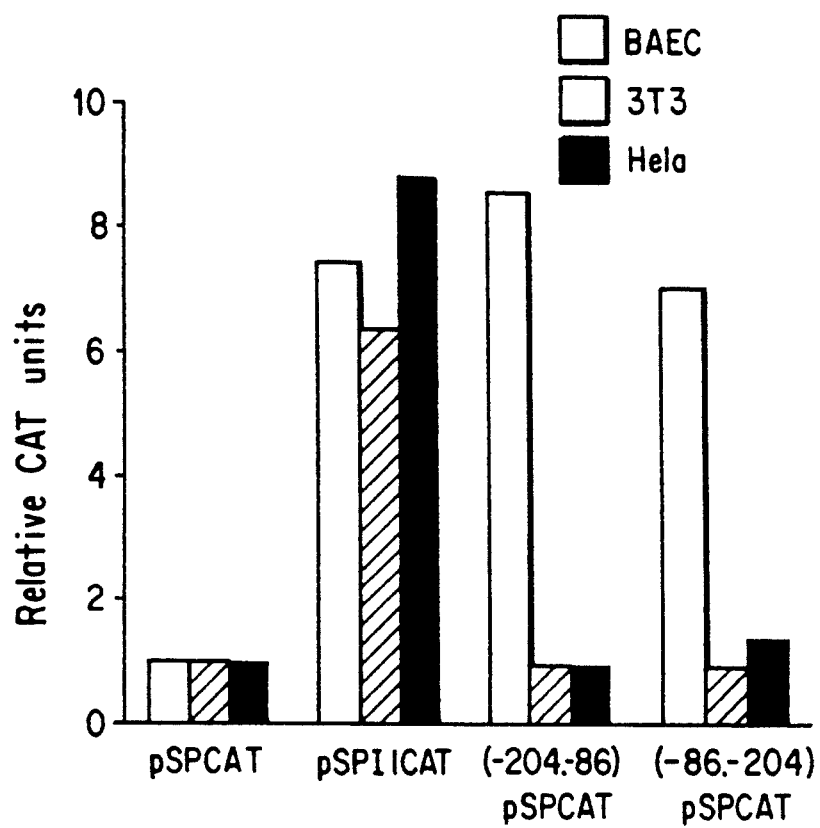

To further explore the possibility that the ET-1 promoter might be sufficient to specify endothelial cell-specific expression and to define the location of the sequences that mediate this aspect of transcriptional regulation, we performed experiments with a CAT fusion construct containing a heterologous promoter. A region of the ET-1 promoter from bp −204 to −86 [SEQ ID NO:4] (FIG. 1A) was cloned in both orientations upstream of a minimal SV40 promoter in the pSPCAT vector. These two constructs [(−204.−86)pSPCAT and (−86.−204)pSPCAT], the pSPCAT vector alone, and pSPCAT containing a non-tissue-specific enhancer (pSPI1CAT) were transfected into BAEC, NIH-3T3 cells, and HeLa cells. The pSPCAT plasmid without additional sequence directed minimal transcription in all cell types tested and the pSPI1CAT construct stimulated the rate of transcription to a similar degree in all cell types (FIG. 4). Constructs containing the ET-1 promoter sequence revealed an increase in transcription of approximately 8-fold in BAEC. This increase was independent of the orientation of the ET-1 DNA. In contrast, the ET-1 constructs did not show enhancement above baseline in the NIH-3T3 fibroblasts or HeLa cells.

These data indicate that sequences between bp −86 and −204 [SEQ ID NO:4] function to increase the rate of transcription in a tissue-specific fashion. The sequences are functional in both orientations and are similar in this regard to other cis-acting sequences that mediate tissue-specific transcription in other cell types (Tsai, S.-F., et al., Nature 339:446–451 (1989); Evans, T., et al., Cell 58:877–885 (1989); Ingraham, H. A., et al., Cell 55:519–529 (1989); Bodner, M., et al., Cell 55:505–518 (1989); Frain, M., et al., Cell 59:145–157 (1989); Dynan, W. S., Cell 58:1–4 (1989); Boulet, A. M., et al., Proc. Natl. Acad. Sci. USA 83:3599–3603 (1986)). Further experiments will be required to determine whether this region of ET-1 5'-flanking sequence will function when placed at a distance from the promoter, and thus whether it is an enhancer type of cis-acting sequence. The restriction fragment used in these heterologous promoter experiments contains both Region A and Region B (FIG. 1A). It includes the CAAT consensus sequence but not the TATAAA consensus sequence. It would seem likely that Region A, Region B, or the combination of these two positive functional regions also account for the tissue specificity of transcription.

The DNA sequences encoded in Regions A and B have been investigated for known enhancer sequences and protein binding sites. Region A contains a sequence (TTATCT) which is similar to the consensus sequence [(A/T)GAT(A/T)(A/G)] known to bind Eryf-1 (Tsai, S.-F., et al., Nature 339:446–451 (1989); Evans, T., et al., Cell 58:877–885 (1989)). Binding of this transacting protein is believed to promote transcription of erythroid-specific genes in developing red cells. However, it seems unlikely that this sequence is functional in this gene, since ET-1 is not transcribed in K562 and HEL cells which are known to produce this trans-acting actor (Tsai, S.-F., et al., Nature 339:446–451 (1989); Evans, T., et al., Cell 58:877–885 (1989)) (M.-E. Lee, K. D. Bloch, and T. Quertermous, unpublished observations). It is possible that the (A/T)GAT(A/T)(A/G) sequence might mediate ET-1 expression in endothelial cells by binding a different protein in this cell type.

Such a paradoxical situation has been described for the octanucleotide sequence ATTTGCAT, which is apparently able to bind two unique proteins (Oct1 and Oct2) that promote transcription of different genes in different cell types (Mitchell, P. J., et al., *Science* 245:371–378 (1989)).

Region B contains an 8-bp AP1 consensus sequence (GTGACTAA) at nucleotides −109 to −102. Similar sequences associated with other genes have been shown to mediate responsiveness to phorbol esters and to serve as a binding site for members of the FOS and JUN protein families (Mitchell, P. J., et al., *Science* 245:371–378 (1989); Dynan, W. S., et al., *Cell* 35:79–87 (1983); Maniatis, T., et al., *Science* 236:1237–1244 (1987); Curran, T., et al., *Cell* 55:395–397 (1988)). Transcription of the ET-1 gene in endothelial cells has been shown to increase in the presence of phorbol esters (Inoue, A., et al., *J. Biol. Chem.* 264:14954–14959 (1989)). Kaprinski et al. (Kaprinski, B. A., et al., *Mol. Cell. Biol.* 9:2588–2597 (1989)), studying the gene coding for the heavy chain of a T-cell surface molecule (4F2HC), found that an AP1 site was an essential element of an enhancer region of this gene. Similar to ET-1, the 4F2HC gene responds to phorbol ester stimulation with an increased rate of transcription (Lindstren, T., et al., *Mol. Cell. Biol.* 8:3820–3826 (1988)). It thus seems possible that a FOS/JUN complex bound to the AP1 sequence in Region B might interact with proteins binding to a specific sequence in Region A to provide full promoter activity.

In summary, promoter regions have been identified, located at sequence −148 to −117 [SEQ ID NO:27 and −129 to −98 [SEQ ID NO:6] of the ET-1 gene, that appear to be necessary for the transcriptional activity in BAEC. When a 119-bp ET-1 genomic fragment containing these two regions was joined to a heterologous promoter, this 119-bp sequence was capable of directing endothelial cell-specific transcription.

Modifications of the above-described modes for carrying out the invention that are obvious to persons of skill in medicine, immunology, hybridoma technology, pharmacology, and/or related fields are intended to be within the scope of the following claims.

All publications and patent applications mentioned in this specification are indicative of the level of skill of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

We claim:

1. An isolated DNA molecule comprising an element of the endothelin-1 (ET-1) promoter (SEQ ID No:1) capable of directing high-level cell-specific expression of a heterologous gene in endothelial cells operably linked to a heterologous gene.

2. The DNA molecule of claim 1 wherein said DNA comprises at least nucleotides 108 to 250 of SEQ ID NO:1.

3. The DNA of claim 1 wherein said element is selected from Region A [SEQ ID NO: 2] and Region B [SEQ ID NO: 3] elements.

4. The DNA of claim 1 wherein said element is Region A [SEQ ID NO: 2].

5. The DNA of claim 1 wherein said element is Region B [SEQ ID NO: 3].

6. A cloning vector comprising the DNA molecule of claim 1.

7. An endothelial cell transformed with the cloning vector of claim 6.

8. A method for directing expression of a gene of interest in vascular endothelial cells, said method comprising:

forming a DNA construct wherein a DNA molecule comprising an element of the endothelin-1 (ET-1) promoter[SEQ ID NO:1] is operably linked to said gene; and transforming endothelial cells with said DNA construct.

9. The method of claim 8, wherein said DNA sequence comprises Region A [SEQ ID NO:2] and Region B [SEQ ID NO:3] DNA elements.

10. The method of claim 8 wherein said DNA sequence comprises nucleotides from about −204 to about −86 [SEQ ID NO:4] of the ET-1 promoter sequence.

11. The method of claim 8 wherein said gene of interest encodes a protein which is a useful for treating thrombosis, thrombolysis, inflammation and immunity disorders.

12. The method of claim 9 wherein said ET-1 promoter element comprises Region A [SEQ ID NO:2] and Region B [SEQ ID NO:3] DNA.

13. The DNA molecule of claim 1 wherein said DNA sequence comprises at least nucleotides 47 to 165 of SEQ ID NO:1.

14. The method of claim 8 wherein said DNA sequence comprises nucleotides from about 108 to about 250 of SEQ ID NO:1.

15. The method of claim 8, wherein said endothelin-(ET-1) promoter element is operably linked to a heterologous promoter.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
        ( A ) LENGTH: 420 base pairs
        ( B ) TYPE: nucleic acid
        ( C ) STRANDEDNESS: single
        ( D ) TOPOLOGY: linear ( i i ) MOLECULE TYPE: DNA ( x i ) SEQUENCE DESCRIPTION: SEQ ID NO:1:

```
GCAGGTTTAG   CAAAGGTCTC   TAATGGGTAT   TTTCTTTTTC   TTAGCCCTGC   CCCCGAATTG      60

TCAGACGGCG   GCGTCTGCCT   CTGAAGTTAG   CAGTGATTTC   TTTCGGGCCT   GGCCTTATCT     120

CCGGCTGCAC   GTTGCCTGTT   GGTGACTAAT   AACACAATAA   CATTGTCTGG   GGCTGGAATA     180

AAGTCGGAGC   TGTTTACCCC   CACTCTAATA   GGGGTTCAAT   ATAAAAGCC    GGCAGAGAGC     240

TGTCCAAGTC   AGACGCGCCT   CTGCATCTGC   GCCAGGCGAA   CGGGTCCTGC   GCCTCCTGCA     300

GTCCAGCTC    TCCACCGCCG   CGTGCGCCTG   CAGACGCTCC   GCTCGCTGCC   TTCTCTCCTG     360

GCAGCGCTGC   CTTTCTCCC    CGTTAAAGGG   CACTTGGGCT   GAAGGATCGC   TTTGAGATCT     420
```

( 2 ) INFORMATION FOR SEQ ID NO:2:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: miscfeature ( B ) LOCATION: 1..32
( D ) OTHER INFORMATION: /note="SEQ 2 CORRESPONDS TO BASES
103 - 134 OF SEQ 1 (REGION A)"

( x i ) SEQUENCE DESCRIPTION: SEQ ID NO:2:

TCGGGCCTGG CCTTATCTCC GGCTGCACGT TG                     32

( 2 ) INFORMATION FOR SEQ ID NO:3:

( i ) SEQUENCE CHARACTERISTICS:
        ( A ) LENGTH: 32 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: miscfeature
        ( B ) LOCATION: 1..32
        ( D ) OTHER INFORMATION: /note="SEQ 3 CORRESPONDS TO BASES
122 - 153 OF SEQ 1 (REGION B)"

( x i ) SEQUENCE DESCRIPTION: SEQ ID NO:3:

CGGCTGCACG TTGCCTGTTG GTGACTAATA AC                     32

( 2 ) INFORMATION FOR SEQ ID NO:4:

( i ) SEQUENCE CHARACTERISTICS:
        ( A ) LENGTH: 119 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: miscfeature
        ( B ) LOCATION: 1..119
        ( D ) OTHER INFORMATION: /note="SEQ 4 CORRESPONDS TO BASES
47 - 165 OF SEQ 1"

( x i ) SEQUENCE DESCRIPTION: SEQ ID NO:4:

CTGCCCCGA ATTGTCAGAC GGCGGCGTCT GCCTCTGAAG TTAGCAGTGA TTTCTTTCGG      60

GCCTGGCCTT ATCTCCGGCT GCACGTTGCC TGTTGGTGAC TAATAACACA ATAACATTG     119

( 2 ) INFORMATION FOR SEQ ID NO:5:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: DNA ( i x ) FEATURE:
        ( A ) NAME/KEY: miscfeature
        ( B ) LOCATION: 1..15
        ( D ) OTHER INFORMATION: /note="SEQ 5 CORRESPONDS TO BASES
108 - 122 OF SEQ 1"

( x i ) SEQUENCE DESCRIPTION: SEQ ID NO:5:

CCTGGCCTTA TCTCC                                        15

( 2 ) INFORMATION FOR SEQ ID NO:6:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear (  i i  ) MOLECULE TYPE: DNA (  i x  ) FEATURE:
    ( A ) NAME/KEY: miscfeature
    ( B ) LOCATION: 1..20
    ( D ) OTHER INFORMATION: /note="SEQ 6 CORRESPONDS TO BASES
        134 - 153 OF SEQ 1"

(  x i  ) SEQUENCE DESCRIPTION: SEQ ID NO:6:

```
GCCTGTTGGT GACTAATAAC                                              20
```